(12) United States Patent
Katchanov et al.

(10) Patent No.: US 11,719,630 B2
(45) Date of Patent: Aug. 8, 2023

(54) RESONANT OPTICAL CAVITY SYSTEM WITH OPTICAL FEEDBACK, SUITABLE FOR DETECTING TRACES OF GAS BY RAMAN SPECTROSCOPY

(71) Applicant: AP2E, Aix-en-Provence (FR)

(72) Inventors: Alexandre Katchanov, San Jose, CA (US); Kevin Jaulin, Venelles (FR); Tim Stoltmann, Aix-en-Provence (FR); Pierre Cholat, Meyrargues (FR); Lucien Lonigro, Les Milles (FR); Bruno Giletta, Marseilles (FR)

(73) Assignee: AP2E, Aix-en-Provence (FR)

( * ) Notice: Subject to any disclaimer, the term of this patent is extended or adjusted under 35 U.S.C. 154(b) by 184 days.

(21) Appl. No.: 17/310,111

(22) PCT Filed: Jan. 15, 2020

(86) PCT No.: PCT/IB2020/050302
§ 371 (c)(1),
(2) Date: Jul. 16, 2021

(87) PCT Pub. No.: WO2020/148671
PCT Pub. Date: Jul. 23, 2020

(65) Prior Publication Data
US 2022/0065778 A1    Mar. 3, 2022

(30) Foreign Application Priority Data
Jan. 18, 2019  (FR) ...................................... 1900454

(51) Int. Cl.
*G01N 21/47*  (2006.01)
*G01J 3/44*   (2006.01)
(Continued)

(52) U.S. Cl.
CPC ............ *G01N 21/47* (2013.01); *G01J 3/4412* (2013.01); *G01N 21/031* (2013.01); *G01N 33/0004* (2013.01)

(58) Field of Classification Search
CPC ................. G01N 21/031; G01N 21/65; G01N 2021/157; G01N 33/0027
See application file for complete search history.

(56) References Cited

U.S. PATENT DOCUMENTS

2005/0073687 A1    4/2005  Morville et al.

FOREIGN PATENT DOCUMENTS

CN    105987895 A  * 10/2016
CN    109580585 A  *  4/2019  ............. G01N 21/01
(Continued)

OTHER PUBLICATIONS

International Search Report and Written Opinion of the International Searching Authority dated Mar. 25, 2020 in connection with International Application No. PCT/IB2020/050302, 15 pages.
(Continued)

*Primary Examiner* — Maurice C Smith (57) ABSTRACT

The disclosure relates to a gas analysis method by Raman spectrometry, the method comprising the steps of generating by a laser source a laser beam sweeping a range of frequencies including a plurality of resonance modes of an optical cavity holding gases to be analyzed; delivering the laser beam into the cavity; extracting from the cavity a feedback beam that is sent adjusted in phase and amplitude to the source; during the frequency range sweeping, detecting light intensity peaks in the laser beam in the cavity, the phase of the feedback beam being adjusted to reduce shape asymmetries of the peaks, the amplitude of the feedback beam being adjusted to reduce intervals of zero intensity between the peaks; and performing a spectral analysis of the light inelas-
(Continued)

tically scattered in the cavity, to determine the composition of the gases to be analyzed.

17 Claims, 5 Drawing Sheets

(51) Int. Cl.
    *G01N 33/00*     (2006.01)
    *G01N 21/03*     (2006.01)

(56) References Cited

FOREIGN PATENT DOCUMENTS

WO     03031949 A1     4/2003
WO     WO-2015160520 A1 *   10/2015   ............. G01N 21/03

OTHER PUBLICATIONS

Michael Hippier, "Cavity-Enhanced Raman Spectroscopy of Natural Gas with Optical Feedback cw-Diode Lasers," Analytical Chemistry, 87, American Chemical Society, 2015 7 pages.

* cited by examiner

RESONANT OPTICAL CAVITY SYSTEM WITH OPTICAL FEEDBACK, SUITABLE FOR DETECTING TRACES OF GAS BY RAMAN SPECTROSCOPY

CROSS-REFERENCE TO RELATED APPLICATIONS

This application is a 371 National Stage of International Application No. PCT/IB2020/050302, filed Jan. 15, 2020, which claims priority to French Patent Application No. 1900454, filed Jan. 18, 2019, the disclosures of which are herein incorporated by reference in their entirety.

BACKGROUND

The present disclosure relates to the analysis of gases by Raman spectrometry. Raman spectrometry is based on the Raman effect which results from an inelastic interaction of a photon with a medium (molecule or crystal). This inelastic interaction is called "Raman scattering". The existence of such an inelastic interaction implies that the medium encountered by the photon has absorbed or provided energy to the photon. This energy transfer is manifested by a frequency shift between the incident photon and the scattered photon following the interaction. When the medium absorbs energy from the photon, the Raman scattering takes a so-called "Stokes shift". When the medium provides energy to the photon, the Raman scattering takes a so-called "anti-Stokes shift". It turns out that these frequency shifts are characteristic of the chemical composition of the medium (crystal, liquid or gas). Raman spectrometry thus consists in focusing a monochromatic light beam on the sample to be studied, forming a Raman spectrum with spectral lines or Raman lines resulting from the Raman scattering, and determining the sample components and their concentrations by comparing the Raman spectral lines of the spectrum to theoretical and experimental data. Indeed, the intensity of the Raman spectral lines is proportional to the number of molecules encountered by the incident beam and to the Raman scattering properties of the encountered molecules, as well as the intensity of the excitation beam. As a result, Raman spectrometry requires a monochromatic laser beam in order to obtain a sufficient spectral resolution, and of sufficient power, considering that the intensity of the Raman lines is much weaker than that of the incident beam. In practice, the required power of the laser source reaches several hundreds of milli-Watts, or even several tens of Watts, which involves the use of powerful, thus expensive and bulky lasers.

Raman spectrometry has been widely developed since the appearance of laser technology, because of its advantages, in particular its capacity to determine the nature of a very large number of different molecules, present in the analyzed medium, without needing to change the laser source, contrary to absorption spectrometry. Shortly after the appearance of the first Raman spectrometers, it was proposed to place the medium to be analyzed in a resonant optical cavity in which the power of a laser beam can be accumulated ("power build-up").

Publication [1] describes a Raman spectrometer for gas detection, in which a sample is placed in an optical cavity excited by an argon ion laser providing a power of 0.5 W, with the optical cavity producing a sample excitation power of 160 W. This system has a detection limit of a chemical species of the order of a few tens of ppm (parts per million). However, argon ion lasers remain too bulky for many applications requiring the use of very compact gas analyzers.

The development of Raman spectrometers has therefore more recently been the subject of intense research towards compacity. Recent progress in the field of optical feedback locking of low power laser diodes to high fineness optical cavities has produced very intense laser beams in these cavities. As an example, publication [2] discloses a resonant optical cavity excited by a laser diode. A small fraction of the laser beam produced by the laser diode is introduced into the optical cavity through one of the cavity mirrors, and undergoes multiple reflections between the cavity mirrors, resulting in a power accumulation. The spectral bandwidth of the beam produced by the laser diode is initially several orders of magnitude larger than the mode width of the cavity. In this situation, the coupling efficiency of the beam produced by a laser diode, typically with a spectral width of 1 to 10 MHz, to a resonant mode of the cavity, with a spectral width of 10 kHz, may be less than a fraction of a percent. Direct injection from a laser diode into a cavity to accumulate power is therefore very inefficient. However, in this publication, a small fraction of the resonant beam circulating in the cavity, and thus having the spectral width of the cavity resonance mode, is extracted from the cavity by one of the cavity mirrors and sent back to the laser diode where it undergoes an amplification of a factor greater than a thousand by stimulated emission. This narrow spectral band beam is then re-injected into the cavity, with a much higher efficiency, and so on. After several cycles, the spectral width of the beam emitted by the laser diode is reduced to the much narrower spectral band of a resonance mode of the optical cavity. In the previous example, the spectral width of the emitted laser beam goes from about 10 Mhz to a few Hertz. The energy emitted by the laser diode can thus be transmitted to the cavity with a high transmission rate, as long as the frequency of the laser beam is sufficiently close to that of a resonance mode of the cavity. The beam emitted by the laser diode can then be frequency-locked to this resonance mode of the optical cavity, and thus remain locked until the intrinsic frequency of the laser diode leaves a locking frequency band including the frequency of the cavity resonance mode. This spectral width reduction and locking effect is called "optical feedback locking". The width of the locking frequency band depends on the fraction of light power that can be extracted from the cavity as an optical feedback beam. Typically, with a feedback coefficient of only −30 dB or less, the locking frequency band can be as wide as the frequency interval between two adjacent longitudinal resonance modes of the cavity, this interval being called the "free spectral range" (FSR) of the optical cavity.

To achieve optical feedback locking, it is necessary to tune the phase of the feedback beam to the phase of the beam travelling in the optical cavity. It is also necessary that the intrinsic optical frequency of the laser diode crosses the locking band of a cavity mode. Several less complex solutions have been proposed to maintain these phase and frequency tunings (see for example publication [3]). However, when the phase and frequency tunings are lost, it is difficult to restore them automatically. In fact, these tuning losses occur frequently, especially in industrial environments with mechanical, thermal and electrical disturbances, making measurements difficult.

U.S. Pat. No. 5,432,610, as well as derivative patents U.S. Pat. Nos. 5,642,375, 5,684,623, 5,835,522 and 6,222,860, disclose Raman spectrometers using a laser diode coupled to an optical cavity. However, it appears that these systems encounter frequent loss of optical feedback problems, leading to intermittent losses of the optical signal. In general, these patents do not indicate how it would be possible to generate a Raman signal that is stable and reproducible, in order to obtain reliable and accurate measurements.

More recently, publications [4] and [5] disclose a Raman spectrometer comprising a linear cavity associated with a complex architecture involving many components. The maintenance of the excitation of the optical cavity in a same mode is achieved by applying to the supply voltage of the laser diode a sawtooth signal of low amplitude, such that the frequency of the laser beam produced by the diode sweeps a certain range of frequencies around the frequency of a single resonance mode of the optical cavity. As a result, the laser beam is always frequency-locked to this single resonance mode, and remains monochromatic. Thus, to ensure that always the same resonance mode is activated, it is sufficient to verify that the cavity transmission peak corresponding to this resonance mode remains in the middle of each up and down ramp of the sawtooth current, and to adjust the diode supply current to maintain this condition. This method also provides a way to adjust the phase of the optical feedback, by observing the symmetry of the transmission peak.

This method appears adequate to produce a persistent and repetitive excitation of the optical cavity in a resonant mode. However, this method remains sensitive to mechanical perturbations: a vibration can cause a loss of phase tuning, which interrupts the resonance of the cavity, until the phase of the optical feedback gets close enough to its optimal value. During this time, it is of course not possible to obtain measurements. Another problem results from the use of a sawtooth signal with rising and falling ramps of equal duration. Indeed, such a signal impedes a duty cycle (ratio between the time during which the locking in the resonance mode of the optical cavity occurs, and the elapsed time) greater than 50%. This is because the locking of the laser diode to a cavity resonance mode occurs not only during the rising ramp of the diode supply current, but also during the shorter descending ramp. In practice, the properties of the optical feedback do not allow achieving a maximum duration transmission peak in the optical cavity during each of the two up and down ramps, while maintaining the symmetry of the transmission peaks and without changing the phase adjustment. Thus, it is necessary to provide a margin in the amplitude of variation of the supply current. This margin leads to limiting the duty cycle to about 50% or less, and therefore to limiting the usable energy supplied by the laser diode.

It is therefore desirable to provide a Raman spectrometry gas analysis system that is compact, stable, robust, and capable of providing high sensitivity measurements. It is also desirable to use the energy produced by the laser source more efficiently.

Patent applications WO03/031949 and WO 2018/060285 disclose optical cavity systems used in the field of absorption spectrometry. In these systems, an optical cavity is excited by a laser diode sequentially tuned by optical feedback to several resonant modes of the optical cavity. These systems seek to minimize the optical power in the cavity, in order to avoid saturation of the absorption lines. These systems have the advantage of offering a very high robustness of operation, and a fast restoration of the optical power in the cavity in case of important disturbance. However, these systems do not seem to be suitable for Raman spectrometry because they are based on the sequential excitation of several modes in the cavity. As a result, the light accumulated in the cavity is not globally monochromatic, but has a periodically varying frequency.

SUMMARY

The present disclosure proposes to adapt the arrangements of these optical cavity systems to the constraints of Raman spectrometry, especially by limiting the mode sweeping range of the optical cavity to below the spectral resolution of the Raman spectrometer, and increasing the accumulated optical power in the optical cavity as much as possible.

Embodiments relate to a method for analyzing gas by Raman spectrometry, the method comprising the steps of: applying a control signal to a laser source to produce a laser beam sweeping a range of frequencies including frequencies of multiple resonant modes of an optical cavity holding gases to be analyzed, the width of the frequency range being less than the resolution of a Raman spectrometer; supplying the laser beam to an entrance of the optical cavity; extracting a feedback beam from the optical cavity; adjusting a phase and an amplitude of the feedback beam; sending the phase and amplitude adjusted feedback beam to the laser source; during sweeping of the frequency range, measuring light intensity variations of the laser beam in the optical cavity, and detecting light intensity peaks in the light intensity variations, each light intensity peak corresponding to a resonance mode of the optical cavity, the phase of the feedback beam being adjusted to reduce a deviation between a median time and the time of occurrence of an apex of one of the light intensity peaks, the amplitude of the feedback beam being adjusted to reduce at least an interval of zero intensity between the light intensity peaks; and acquiring, with a spectrometer sensor, measurements of the spectrum of light inelastically scattered by the laser beam in the optical cavity to determine the nature and/or concentration of gases in the optical cavity.

According to an embodiment, the control signal for the laser source has a periodic shape, and the spectrometer sensor, comprising a plurality of photosensitive cells, receives a portion of the inelastically scattered light and is controlled to operate exposure phases alternating with readout phases during which spectrum measurements are produced by the photosensitive cells; the method comprising, during each exposure phase, the following steps: obtaining an integral value of measurements of light intensity of the laser beam in the optical cavity, and/or of light intensity of a portion of the light elastically scattered by the laser beam in the optical cavity; and normalizing each of the spectrum measurements obtained at the end of the exposure phase as a function of the integral value, to produce a normalized spectrum.

According to an embodiment, the exposure phases have a duration equal to a multiple of the period of the control signal of the laser source, plus a fraction of that period, the start of each exposure phase being synchronized with the control signal of the laser source.

According to an embodiment, each exposure phase is started and interrupted during periods when no light is present in the optical cavity.

According to an embodiment, the method comprises the steps of: periodically turning off power to the laser source to measure a dark current in a photodetector providing the measurements of light intensity variations of the laser beam in the optical cavity; and correcting the measurements of light intensity variations of the laser beam in the optical cavity using an average of the dark current measurements.

According to an embodiment, the power interruptions of the laser source are performed outside the exposure phases.

According to an embodiment, the method comprises the steps of: turning off the power to the laser source during an interruption phase extending over at least one consecutive exposure phase; and for each light sensitive cell of the spectrometer sensor: measuring a dark current during the interruption phase, correcting a stored average dark current for the photosensitive cell based on the dark current measurement obtained for the photosensitive cell, and correcting each spectrum measurement provided by the photosensitive cell according to the stored average dark current for the photosensitive cell, wherein the measurement of dark current may be preceded by several measurements not taken into account to erase the photosensitive cells.

According to an embodiment, the laser beam provided at the entrance of the optical cavity and the feedback beam are transmitted through the same optical path between the laser source and the entrance of the optical cavity.

According to an embodiment, the amplitude of the feedback beam is adjusted by an adjustable Faraday isolation module installed in the optical path between the laser source and the entrance of the optical cavity, the Faraday isolation module attenuating the amplitude of the feedback beam and passing the laser beam from the laser source.

According to an embodiment, the Faraday isolation module is servo-controlled as a function of light intensity measurements of the laser beam in the optical cavity, to minimize the zero intensity intervals between light intensity peaks, wherein the servocontrol of the Faraday isolation module can be achieved by acting on its temperature.

Embodiments may also relate to a device for analyzing gas by Raman spectrometry, comprising an optical cavity into which a laser beam issued by a laser source is introduced, wherein the device is configured to carry out the method defined above.

According to an embodiment, the laser source is configured to sweep the frequency range without mode hopping.

According to an embodiment, the optical cavity is V-shaped and comprises a coupling mirror forming the entrance to the optical cavity, and two cavity end mirrors, the cavity end mirrors having a reflectivity greater than or the same as the coupling mirror.

According to an embodiment, the mirrors forming the optical cavity have radii of curvature adapted to adjust the shape of the beam within the optical cavity to a zone for collecting light scattered in the cavity under the effect of the laser beam.

According to an embodiment, light scattered in the optical cavity is observed through one of the cavity end mirrors, the cavity end mirrors having a coating with a maximum reflectance for the reflected beam in each of the resonance modes of the optical cavity, and having a maximum transmittance for at least one Stokes line of the Raman lines.

According to an embodiment, the laser source is one of the following types: a distributed feedback laser diode, a distributed Bragg reflector laser diode, a Fabry-Perot type diode stabilized by a volume or holographic Bragg diffraction grating, or by a narrow band filter, a laser associated with a device for adjusting the emission frequency, a surface emitting laser with a vertical cavity, coupled to a dielectric membrane mirror.

According to an embodiment, the device comprises an actuator coupled to a mirror for altering an optical path length between the laser source and the entrance to the optical cavity, to adjust the phase of the feedback beam.

BRIEF DESCRIPTION OF THE DRAWINGS

Exemplary non-limiting embodiments of the disclosure will be described in the following in relation to the attached drawings among which.

DETAILED DESCRIPTION

Figure 1:
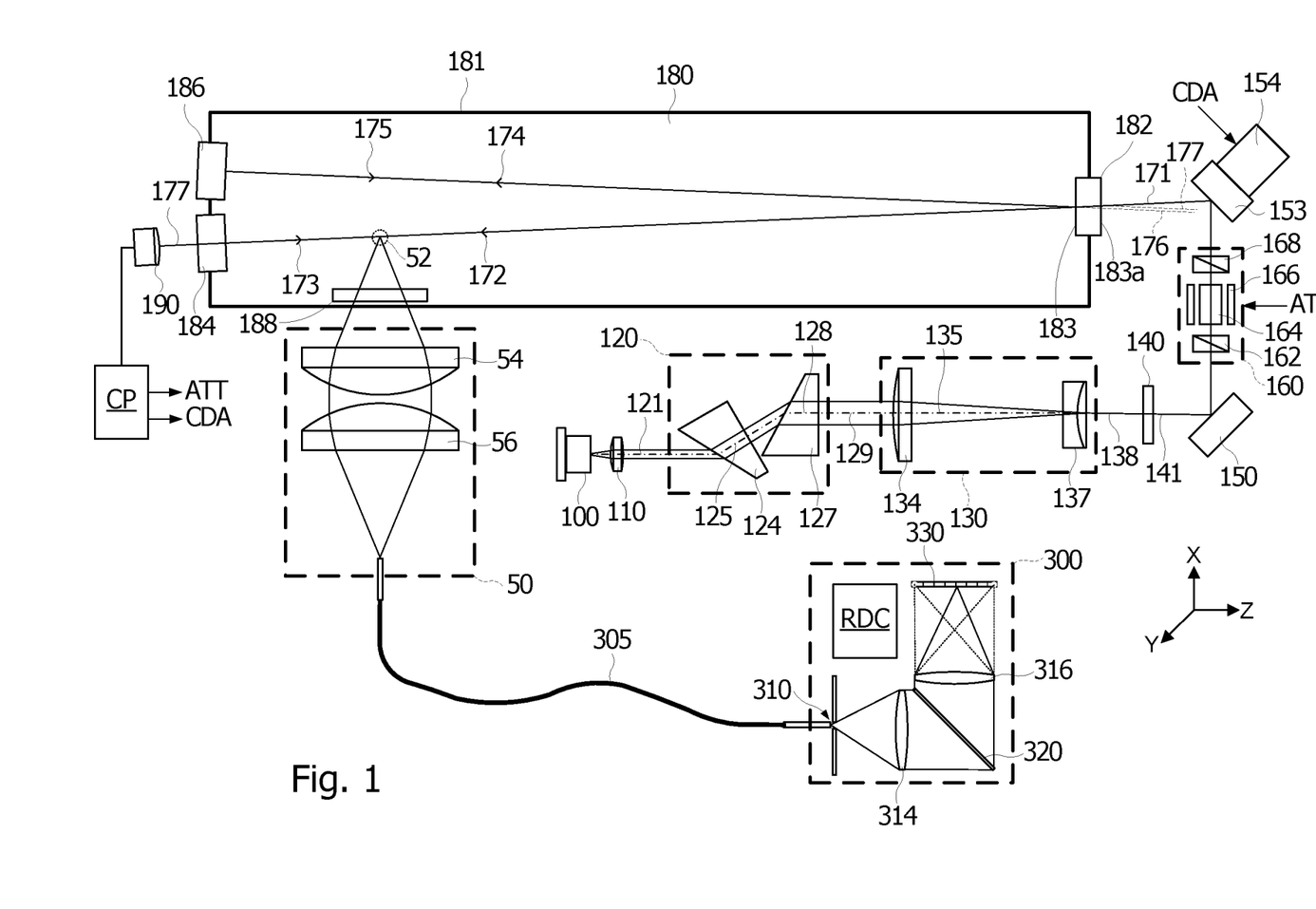
FIG. 1 schematically represents a Raman spectrometry gas analysis system, according to an embodiment.

FIG. 1 represents a Raman spectrometry gas analysis system, according to an embodiment. The gas analysis system includes a laser source 100, an optical module 120 for shaping the laser beam emitted by the laser source, an optical module 130 for resonance mode tuning, an optical module 160 for optical feedback attenuation, an optical cavity 180, a photodetector 190, and an optical device 50 for collecting a portion of the light scattered by gases present in the optical cavity 180 through the effect of the laser beam in the optical cavity, the optical device 50 being coupled to an input 310 of a Raman spectrometer 300.

The two-armed, V-shaped optical cavity 180 includes a cavity body 181 bounding the cavity 180, an input or coupling mirror 182, and two cavity end mirrors 184, 186, all three mirrors being attached to the cavity body 181. The cavity body 181 is configured to accept a flow of gases to be analyzed, and to propagate light between the mirrors 182, 184, 186. The cavity body 181 may be made, for example, of stainless steel.

The laser source 100 is configured to emit a light beam in a single longitudinal mode, in the ultraviolet range, in the visible range of the near infrared. The laser source 100 also has the ability to change the frequency of the emitted laser beam, for example without mode hopping, in response to variations in one of its control parameters, for example its supply current or temperature, or other parameters dependent on the structure of the laser source. Furthermore, the range of variation of the emission frequency of the laser source 100, extends over more than the width of several free spectral ranges FSR of the cavity 180. The beam from the laser source 100 is emitted in a Z direction. FIG. 1 is located in an XZ plane, with the Y direction perpendicular to the XZ plane.

The laser source 100 may be, for example, a Distributed Feed Back (DFB) type laser diode. It is possible to use other laser sources, such as a DBR (Distributed Bragg Reflector) laser diode. The laser source can also be a Fabry-Perot diode stabilized by an external frequency selection element, such as a Volume Bragg Grating (VBG), a diffraction grating, or a narrow band filter. The laser source may also be a laser associated with a complex emission frequency adjustment device, or a Vertical Cavity Surface Emitting Laser (VCSEL) coupled to a dielectric membrane mirror, whose emission frequency can be adjusted by a voltage applied between the laser substrate and the mirror.

The beam emitted by the laser source 100 passes through an optical collimation module 110 reducing the divergence of the emitted beam, both in two directions perpendicular to the beam propagation direction. The collimation of the emitted laser beam is conventionally implemented in spectrometry using a laser diode, to facilitate the delivery of the laser beam to an absorption cell and to a photodetector at the cell output. In Raman spectrometry, based on the use of an optical cavity, the conformation of the laser beam is realized more accurately. Indeed, to obtain an efficient light energy transfer, the laser beam is tuned to the fundamental resonance mode of the cavity, which requires to adjust the amplitude and phase distributions of the laser beam to make them as close as possible to those of the fundamental resonance mode of the cavity. In the embodiment shown in FIG. 1, the mode tuning is performed by the optical modules 110, 120 and 130.

The module 110 may be a single lens that may be aspherical, or a double acylindrical lens. The module 110 may also be a combination of several more or less complex lenses or other optical components.

Many laser diodes produce beams that have an elliptical shape with high eccentricity and/or high astigmatism. The collimated laser beam 121 at the output of the module 110 can therefore have very different widths and divergences depending on the direction considered. The collimated laser beam 121 exiting module 110 is then processed by the optical shaping module 120 configured to produce a beam having a substantially circular shape. According to an embodiment, the optical shaping module 120 includes a pair of anamorphic prisms 124, 127, that expand the beam 121 in one direction. According to the orientation of the prisms 124, 125 shown in FIG. 1, the beam 121 exiting the optical module 110 has an elliptical cross-section (in the XY plane) with the longest axis oriented along the Y direction. The two prisms 124, 127 expand the beam in the X direction to make the beam widths in the X and Y directions as close as possible to each other. As an example, the eccentricity of the laser beam produced by the laser source is 2.8. However, laser diodes in the visible range can provide a laser beam with an eccentricity of 4.

According to another embodiment, the optical module 120 may be made with cylindrical lenses.

The shaped laser beam 129 output from the optical module 120 is then processed by the resonant mode tuning optical module 130. The module 130 is configured to adjust the spatial parameters of the beam 129 to be close to the spatial parameters of the fundamental mode beam of the optical cavity 180 (mode tuning). This mode tuning condition may be achieved when the amplitude and phase distributions in the X and Y directions of the beam 171 at the input mirror 182, coincide or are very close to those of the beam 172 corresponding to the fundamental mode of the cavity. The optical module 130 may include one or more lenses or a combination of different optical components. In the example shown in FIG. 1, the optical module 130 includes two spherical lenses 134, 137.

The beam 138 exiting the optical module 130 is directed to the input mirror 182 of the optical cavity 180 by two mirrors 150, 153, so that the beam 171 reflected by the mirror 153 is collinear with the image of the fundamental mode beam 172 present in the cavity 180. The mirror 153 is mounted on an actuator 154 such as a piezoelectric transducer, allowing to adjust the optical path length between the output of the laser source 100 and the coupling mirror 182 at the input of the optical cavity 180, and thus to adjust the phase of the feedback beam from the cavity 180, originating from the cavity end mirror 184. In this way, the conditions for optical feedback locking can be satisfied.

Between the mirrors 150 and 153, the optical module 160 adjusts the attenuation of the optical feedback intensity. The function of the module 160 is to adjust the intensity ratio between the feedback beam and the incident beam from the laser source 100 to an optimal value, as long as the feedback lock bandwidth is close to but not greater than the free spectral range FSR. The optimal value of the feedback beam intensity depends on the characteristics of the mirrors 182, 184, 186 forming the optical cavity 180, the characteristics of the laser source 100, and the coupling efficiency between the laser source and the optical cavity. Typically, the attenuation ratio required to achieve this optimum value is between 25 and 35 dB. It turns out that the optimal value of the feedback beam intensity is sensitive to minute variations, to such an extent that it varies within a single manufacturing batch. This optimal value also varies over time, especially due to the ageing of the components of the gas analysis system, and to intra-cavity losses due to the presence of certain gases.

In theory, any attenuator with an adjustable transmission coefficient can be used. Thus, the attenuator module 160 may be, for example, a neutral density filter, or even a pair of nearly crossed polarizers. However, such polarizers may cause a significant loss of power of the beam injected in the cavity, which is not desirable in a Raman spectrometry system. In practice, it is preferable not only to adjust the locking range of the optical feedback, but also to inject as much light power as possible into the cavity, which is not the case in the prior art systems (e.g., disclosed in patent application WO 03/031949).

The beam 172 resulting from the transmission of the beam 171 by the coupling mirror 182, is reflected by a first mirror 184 of the cavity end mirrors. The beam 173 reflected by the mirror 184 is reflected on the coupling mirror 182. The beam 174 reflected from the coupling mirror 182 is reflected back to a second mirror 186 of the cavity end mirrors, which reflects a beam 175 back toward the coupling mirror 182. The portion of the cavity beam 173 originating from the mirror 184 and passing through the coupling mirror 182 constitutes the feedback beam. The portion 176 of the beam 175 originating from the mirror 186 and passing through the coupling mirror 182 has the same direction as the portion 177 of the incident beam 171, which originates from the laser source 100 and is reflected directly by the coupling mirror 182 without entering the cavity.

The beam 172 entering the optical cavity 180 excites one of the cavity mode systems. One of the cavity mode systems is polarized in the plane of incidence (XZ) of the coupling mirror 182, and another of these cavity mode systems is polarized perpendicular to the plane of incidence YZ. As a result, to excite one of these cavity mode systems, the transmission axis of the output polarizer 168 of the attenuation module 160, is oriented parallel to the X or Y axis. The transmission axis of the input polarizer 162 is thus oriented approximately 45° to the XZ plane. This does not coincide with the polarization of the incident beam 138 from the module 130. The polarization of the beam 138 is therefore rotated by an angle of approximately 45°, for example by means of a waveplate 140 arranged between modules 130 and 160. The output beam from the waveplate 140 thus has a polarization corresponding to the orientation of the input polarizer 162.

The photodetector 190 observes the beam inside the optical cavity 180, through the cavity end mirror 184. The photodetector 190 is for example a photodiode. The signals from the photodetector 190 are processed and analyzed by a processor CP configured to generate signals ATT and CDA for controlling the actuator 154 and the attenuation module 160.

The laser beam crossing the optical cavity, including parts 172 to 175, is used as a source to produce Raman scattering. The scattered light is collected by optical module 50 comprising two lenses 54, 56 of large numerical aperture, which transmit an image of the scattered light out of the cavity body 181 to an area 52 for collecting the scattered light of the cavity. The optical module 50 is coupled to the input of a Raman spectrometer, either directly or via an optical link 305. The optical link 305 may be an optical fiber having a suitable diameter or a bundle of optical fibers.

The Raman spectrometer may classically include an entrance slit 310 coupled to a collimating lens 314 having a large numerical aperture, a diffraction grating 320, a lens 316, and a spectrometer sensor 330 for producing a spectrum of the light issued from the diffraction grating 320. The light beam entering through the slit 310 is transmitted to the diffraction grating 320 through the lens 314. The light beam from the diffraction grating 320 is transmitted to the sensor 330 through the lens 316. The sensor 330 comprises an array of several hundred light-sensitive cells that receive the light transmitted by the lens 316 through a filter that distributes the received wavelengths over the light-sensitive cells of the sensor 330, so that each cell of the sensor receives only a reduced range of wavelengths belonging to the wavelength band corresponding to the spectrum to be produced. The filter may be, for example, a Fabry-Perot filter, or of a variable linear filter. With such a filter, the wavelengths transmitted to the photosensitive cells of the sensor 330 can exclude the wavelength band of the laser beam in the optical cavity, so that the photosensitive cells receive only the light scattered inelastically in the cavity, i.e., the Raman spectrum.

The spectrum generated by the sensor 330 can be analyzed using spectral analysis techniques known in Raman spectrometry, to determine the nature and/or concentration of the gases present in the optical cavity. These spectral analysis techniques may include detecting and measuring, in the produced spectrum, frequencies and amplitudes of Raman lines from which the nature and possibly the concentration of gases present in the optical cavity can be deduced.

The coupling mirror 182 includes on its surface facing the interior of the cavity 180 a dielectric coating 183 having a high reflection coefficient R (close to 1). The surface of the mirror 182 facing the outside of the cavity may be covered with an anti-reflection coating 183a. Typically, the value 1-R is selected in the range of a few ppm to several hundred ppm. In some embodiments, the value 1-R may even be a few percent.

According to an embodiment, the cavity end mirrors 184, 186 are identical to the mirror 182. As a result, at a peak of light intensity observed in the cavity, the laser beam traveling through the cavity exits the cavity in four directions, each time it encounters one of the mirrors 182, 184, 186.

According to another embodiment, the cavity end mirrors 184, 186 have a much higher reflectivity than the mirror 182. This arrangement reduces the energy losses due to transmission of the laser beam traveling through the cavity by the cavity end mirrors 184, 186, and also increases the light power accumulation in the optical cavity 180 up to a factor of 4, and a corresponding increase in the Raman signal intensity.

The gain in accumulated light power in the cavity can be as high as four by canceling the significant losses of light power due to the absorption of the gases filling the cavity 180 and when the mirrors 184, 186 at the end of the cavity have very high reflection coefficients, much higher than their transmission coefficients. In this case only, a small part of the light power exits the cavity through the mirrors 184, 186, and the accumulation of light power in the cavity is such that the beam 176 exiting the cavity through the coupling mirror 182, and the beam 177 reflected directly thereby, are collinear and have substantially identical powers. As the beams 176 and 177 have opposite phases, their combined power is close to zero. Thus, all the power transmitted by the laser source to the cavity exits the cavity in one direction instead of four, the other three beams exiting the cavity having a negligible intensity. This arrangement achieving the injection in the optical cavity of all the available energy supplied by the laser source, while avoiding losses, is called "impedance tuning" in the theory of resonant optical cavities.

To obtain usable Raman signals, it may be advantageous to improve the coupling between the light scattered in the optical cavity 180 and the entrance slit 310 of the Raman spectrometer. The entrance slit of a conventional Raman spectrometer has a width between 25 and 100 µm and a height of a few millimeters. This entrance slit is placed in the focal plane of a collimating lens with a low aberration and a numerical aperture of about 0.4. It may therefore be desirable to have a laser beam in the optical cavity having, in the collection area 52, a diameter such that its image by the optical device 50 coincides with the entrance slit 310 of the spectrometer 300. Or conversely, to optimize the collection of scattered light, it may be desirable for the diameter of the laser beam in the collection area 52 to correspond to the image by the optical device 50, of the width of the entrance slit 310.

According to an embodiment, the matching of the beam diameter in the collection area 52 in the optical cavity 180 to the width of the spectrometer entrance slit 310 is achieved by an appropriate choice of the radius of curvature of the cavity mirrors 182, 184, 186. As is known, for a given entrance slit height, and a given numerical aperture of the spectrometer entrance optics, the magnification ratio of the optical device 50 can be determined, and the optimal focusing parameters of the laser beam in the cavity can be calculated (see, for example, ref. [1]). For instance, considering the parameters of a conventional compact Raman spectrometer, such as the one designated by WP 785L, designed to operate at the excitation wavelength of 785 nm, having a numerical aperture of 0.38, and an entrance slit height of 0.6 mm, the optimal diameter of the excitation laser beam in the cavity is 24.5 µm. The choice of such a diameter achieves a maximum intensity in the scattered Raman light, and thus in the Raman signal. This implies that if the entrance slit of the spectrometer has a width of 25 µm, and if the 785 nm excitation laser beam is focused to a diameter of 24.5 µm, then the Raman signal that can be observed has the highest possible intensity. However, in a conventional spectrometry system, with optical feedback locked to a V-shaped optical cavity, with three cavity mirrors having the same radius of curvature of 400 mm and optical cavity arms of 200 mm in length, the diameter of the laser beam in the cavity locally reaches at least 418 µm, which corresponds to 16.7 times the optimum width. This implies a 10-fold loss compared to what could be obtained when the coupling is optimal. If the radius of curvature of the cavity mirrors 182, 184, 186 is reduced, for example to 20 mm, by placing them so as to reduce the cavity arms to 30 mm, the diameter of the laser beam in the optical cavity, as seen by the optical device 50, increases locally to a minimum value of 94 µm, which corresponds to 4 times the optimum width. Theoretically, it would be possible to reduce the radius of curvature of the cavity mirrors to locally reduce the diameter of the laser beam in the cavity to the optimum value of 24.5

µm, but this would imply unrealistic values for the radius of curvature of the cavity mirrors (0.7 mm) and for the length of the cavity (1.05 mm).

According to an embodiment, the diameter of the excitation laser beam in the cavity is locally reduced by selecting three mirrors of distinct radii of curvature and different V-cavity arm lengths. According to an exemplary implementation, mirrors 182 and 184 have a fixed radius of curvature of 20 mm and are spaced 30.3 mm apart, and mirror 186 is flat and 160 mm away from the input mirror 182. This configuration results in an excitation laser beam in the cavity having a local narrowing of 26 µm in diameter. The narrowing of the excitation laser beam is located at a distance of 20 mm from the mirror 184. This configuration achieves a much better coupling of the scattered light at the entrance of the spectrometer, and thus a much better measurement sensitivity.

To illustrate the operation of the analysis system of FIG. 1, FIGS. 2 to 4 represent, at the same time scale, time diagrams of a control signal waveform 200 supplied to the laser source 100, a signal 220 from the photodetector 190 (representative of the light intensity accumulated in the optical cavity 180), and a signal 240 for controlling the sensor 330.

In the following description, it is assumed that the emission frequency of the laser source is controlled by its supply current. Of course, if the laser source used is controlled by another parameter, the provisions described below regarding the supply current also apply to that control parameter.

Figure 2:
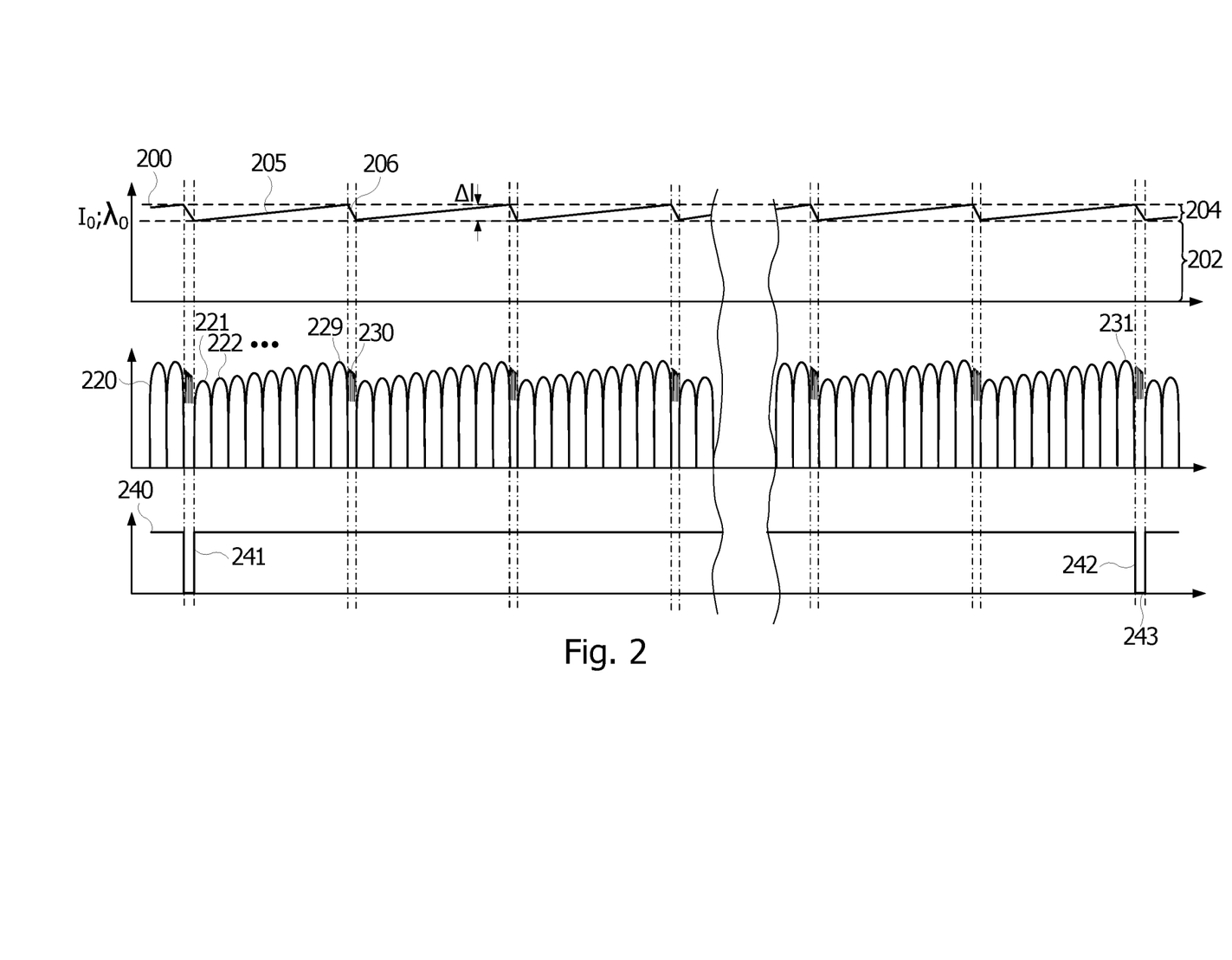
FIGS. 2 through 5 represent time diagrams of signals observed in the gas analysis system of FIG. 1.

According to an embodiment, the control signal 200 for the laser source 100 is a supply current 200 including a DC component 202, and a variable component 204, such as a sawtooth component, which is added to the DC component 202. The DC component 202 is set to a value TO close to the nominal current for generating a laser beam 121 having a power close to the nominal value of the laser source 100. The variable component 204 has a variation amplitude ΔI, and rising phases or ramps 205 separated by falling phases or ramps 206 of shorter duration. During the rising phases 205, the intrinsic wavelength of the laser beam 121 emitted by the laser source 100 (in the absence of feedback) increases from a minimum value λ0 corresponding to the current TO. During the falling phases 206, the intrinsic wavelength of the laser beam 121 decreases to the minimum value λ0.

According to an embodiment, the duration of the descending phases 206 is reduced so that the emission frequency of the laser source varies sufficiently rapidly during these phases, whereby no accumulation of light power has time to form in the optical cavity 180.

According to an embodiment, the variation amplitude ΔI of the supply current to the laser source 100 is defined so as to successively reach several consecutive resonance modes of the optical cavity 180. Thus, the signal 220 that is obtained in a situation where the feedback beam has the required amplitude and phase, exhibits several light intensity peaks 221, 222 ... 229, during each of the rising phases 205 of the supply current 200. Furthermore, it can be observed that the optical power accumulated in the cavity increases with the supply current. The existence of these peaks 221-229 shows that the laser source 100 successively locks onto several resonance modes of the cavity 180. With the implementation of such a supply current for the laser source 100 ensuring the sweeping of at least two cavity modes, light intensity peaks appear regardless of the value of the first intrinsic wavelength emitted by the laser diode, and virtually regardless of the phase of the optical feedback beam, with the exception of a small interval around the point where the phase is in opposition to the optimum phase. It is thus possible, following a sudden loss of phase lock, to implement the following restoration process.

When the phase of the feedback beam is incorrect, the maximum amplitude of the light intensity peaks in the cavity remains below the maximum value reached when the phase is adjusted to its optimum value. When the observed maximum amplitude of the light intensity peaks drops below a threshold value set to a value less than the maximum value reached when the phase is adjusted to its optimum value, the processor CP starts a ramp covering a phase of at least 4n, and observes the laser beam in the cavity until the phase tuning condition is detected again. In practice, the phase tuning restoration typically takes a few periods of the variable component 204, and the Raman signal can be acquired without interruption.

Once one of the peaks 221-229 is observed using the photodetector 190, the phase of the feedback beam can be fine-tuned, with the optimum value of the phase being reached when the time of occurrence of the apex of at least one of the peaks 221-229 is in the middle of the interval between the start and end times of the peak. The fine tuning of the phase of the feedback beam can be performed by analyzing the derivative of the signal 220, the time of occurrence of the apexes corresponding to the times when the derivative of the signal 220 is zero, and the start and end times of the peaks corresponding to the times when the derivative of the signal 220 is maximum.

Then, the centering of the peaks 221-229 can be adjusted with respect to the rising phases 205 of the current 200 by acting on the value of the constant component TO, or on the temperature of the laser source 100 and on the amplitude ΔI of variation of the current 200. The absence of one of the peaks 221-229 (period when the power in the cavity is zero) may indeed lead to some instability of the light power accumulated in the cavity. In FIG. 2, the centering is optimal insofar as the start of the first peak 221 coincides with the beginning of the rising phase 205, where the end of the last peak 229 coincides with the end of this phase, and therefore where the maximum number of peaks during a rising phase 205 is reached. Varying the value of the DC component I0 (202) affects the start time of the first peak 221 and varying the amplitude ΔI affects the coincidence between the end time of the last peak and the end of the rising phase 205. Such corrections may in fact be required anyway, in particular because of the ageing of the laser source, leading to variations in its characteristics (wavelength of the emitted beam as a function of the supply current, or parameters characterizing the feedback).

During the descending phases 206 of the supply current 200, a sequence 230 occurs where the resonant modes are rapidly swept, due to the shorter duration of the descending phases. The power accumulated in each mode is therefore less than during the rising phases. It can be observed in FIG. 2 that the length of the descending phases 206 has been enlarged for clarity, to show that during these phases, the laser source 100 sequentially locks onto the same cavity modes as during the rising phases 205, but in a reverse order. According to an embodiment, the descending phases 206 are shortened to the point that the sweeping of the cavity modes is performed too quickly for the laser source to lock onto the cavity modes. This configuration avoids pollution of the Raman signal by transient signals that could appear due to mode locking during the descending phases 206, and that could affect the locking process during the rising phases 205.

Unlike prior art solutions using a laser source supply current with a variation amplitude defined so as to reach a single cavity resonance mode, there is no need to center the rising phase of the supply current on a resonance mode, since the variation amplitude ΔI of the laser source supply current systematically achieves several of the cavity modes. It also appears that this method of exciting an optical cavity is not very sensitive to mechanical disturbances, as the locking on the different resonance modes of the cavity is very robust. In fact, the locking of the laser source 100 to a mode of the optical cavity can be lost only when the photodetector 190 does not detect a signal in the cavity, in case of a significant phase shift of the feedback beam. When the intensity of the peaks measured by the photodetector 190 is below a certain threshold value, the phase of the feedback beam is controlled to perform a rapid sweep from the minimum to the maximum value of the phase, until the onset of the peaks becomes visible. The locking process can then occur. For this reason, in cases where a loss of lock occurs, the restoration of a lock condition is fast and easy.

It should be noted that the phase of the feedback beam may be adjusted by changing the optical path length between the laser source and the coupling mirror 182, for example by controlling a small displacement of the mirror 153 by means of the transducer 154. Other known means of adjusting the optical path length may also be used, such as an electro-optical modulator as described in WO 2018/060285.

The optimum value of the amplitude ΔI of variation of the supply current for the laser source 100 can be determined from the current shift δI required to switch from one resonance mode to another, and the desired number of modes Nm to be excited. Thus, the amplitude ΔI can be obtained using the following equation:

$$\Delta I = Nm \times \delta I + \delta Is \quad (1)$$

where δIs represents an additional stability current such that: 0<δIs <δI.

It can also be observed that the previously described method of exciting the optical cavity 180, consisting of sweeping more than one resonance mode of the cavity, seems to contradict the fact that Raman spectrometry requires a monochromatic laser beam. If this condition is not met, the resolution of the measurements is degraded. Indeed, if several resonance modes are excited during each phase 205, 206 of the laser source supply current 200, the excitation of the cavity 180 is not monochromatic, but has the form of a train of pulses of different wavelengths. For example, if a CCD (Charge-Coupled Device) array with 1024 to 2048 light-sensitive cells (pixels) is used as the sensor 330 for the Raman spectrometer. Such a sensor can cover a Raman frequency band, for example from 2000 to 4000 cm−1. A spectrum picture element should be provided by at least three pixels of sensor 330. In an extreme case where a spectrum picture element corresponds to a single pixel, the spectral width of a spectrum element may not exceed 2 to 4 cm−1. Furthermore, the frequency shift between two resonant modes in a V-cavity with 20 cm branches is 0.0125 cm−1. This means that several dozen cavity resonance modes can be swept during a single ramp 205 of the variable component 204 of the supply current 200 for the laser source 100, knowing that these resonance modes cannot be distinguished with a spectral resolution of at best 2 cm−1. As a result, the laser beam present in the cavity 180 during a ramp 205 excites cavity modes that remain in a frequency range having a width well below the resolution of the sensor (i.e., 4 cm−1).

The gas analysis system described above has a high stability and is able to maintain the lock condition of the laser source indefinitely, except in case of a very strong mechanical disturbance. In the case of such a disturbance, the restoration of the lock condition is very fast (less than one second). Due to the high power that can be accumulated in the optical cavity, the spectrometer has a high sensitivity and thus offers a high accuracy in the determination of gas concentrations present in the optical cavity.

In the context of a Raman spectrometer, it is preferable to use an attenuator that transmits the full power of the beam from the laser source 100, while attenuating the feedback beam with an attenuation factor adjusted to the optimum value. According to an embodiment, the attenuator module 160 includes a Faraday isolation module having an input polarizer 162, a Faraday optical medium 164, and an output polarizer 168. The Faraday optical medium 164 is placed in a magnetic field, for example produced by a permanent magnet 166, collinear with the direction of propagation of the beam from the laser source 100. When the Faraday rotation applied by the optical medium 164 to the incident beam from the input polarizer 162 is equal to 45° and corresponds to the orientation of the output polarizer 168, the incident beam experiences a small power loss. In contrast, the feedback beam passing through the module 160 in the reverse direction is polarized perpendicular to the transmission axis of the input polarizer 162. Thus, if the optical medium 164 does not produce depolarization, and if the polarizers are ideal, the feedback beam is fully cancelled. In other words, the attenuation ratio is zero. The attenuation ratio is adjusted by adjusting the polarization angle difference between the two polarizers 162, 168. The purpose of this adjustment is to bring the width of the peaks 221-229 to an optimum value, in order to reduce the intervals of zero intensity between the peaks of light intensity, or at least one of these intervals.

Usually, this adjustment of the feedback beam intensity is done from time to time, for example during a start-up phase of the system. Indeed, the properties of the cavity and the laser source can vary slowly with time, leading the feedback beam intensity to deviate from its optimum value. However, it may be desirable to dynamically adjust the intensity of the feedback beam.

Furthermore, it turns out that the magnetic properties of Faraday isolators, such as the magnetic field and the Verdet constant, vary with temperature. The internal temperature of the Raman spectrometer can be held constant. In a disturbed environment, the spectrometer can also experience changes in ambient temperature, which can impact the temperature distribution inside the spectrometer, even if the temperature inside the cavity 180 is held constant. In fact, the temperature of the attenuation module 160 can vary, which can also impact the intensity of the feedback beam, which can deviate from its optimal value. A decrease in the intensity of the feedback beam can thus lead to a loss of sensitivity of the spectrometer. On the other hand, an increase in the intensity of the feedback beam may cause the peaks 221-229 to broaden to the point of exceeding the distance between adjacent cavity modes, and thus cause the spectrometer to stop operating due to a loss of cavity mode. A safety margin may be introduced by setting the intensity of the feedback beam to a value less than the optimal value. However, this solution has the effect of reducing the power accumulated in the cavity and thus the sensitivity of the spectrometer.

According to an embodiment, a heating device is coupled to the attenuation module 160 to compensate for undesirable variations in the temperature of the module 160, based on the width of the light intensity peaks in the cavity. The heating device may be, for example, a Peltier cell or a heater band wrapped around the module 160. Furthermore, the initial optimal intensity of the feedback beam is set to a value corresponding to a temperature of the module 160 that is higher than the set temperature of the interior of the spectrometer. Furthermore, the module 160 is configured so that maximum isolation is achieved at a higher temperature. With such an initial configuration, the width of the light intensity peaks 221-229 in the cavity is monitored using the signal 220 provided by the photodetector 190. If the width of these peaks 221-229 needs to be reduced, the temperature of the module 160 is reduced, by lowering the supply voltage to the heater, thereby increasing the intensity of the feedback beam, and vice versa. Thus, the heater can be servo-controlled to maintain the width of the peaks 221-229 at an optimum value, to reduce at least one, and preferably all, of the zero intensity intervals between the light intensity peaks.

Conventionally, the sensor 330 is controlled to operate exposure phases alternating with readout phases during which frequency spectrum measurements are achieved by the photosensitive cells of the sensor. To avoid beat phenomena, it may be advantageous to synchronize the control signal of the laser source with the spectrometer.

According to an embodiment, the exposure phase of the sensor 330, i.e., the integration phase of photons entering the sensor 330, is timed to an integer number of periods 205-206 of the supply current 200 for the laser source 100. The start of the exposure phase is synchronized with the supply current 200, for example with the start of a rising ramp 205 of the supply current. FIG. 2 shows a control signal 240 for the sensor 330. Pulses 241 and 242 of signal 240 control the start and end of the exposure phase of sensor 330, respectively. The rising edge of pulses 241, 242 is timed to the start of a rising ramp 205 of supply current 200, and the falling edge of pulses 241, 242 is timed to the end of another rising ramp 205 of supply current.

At the end of the exposure phase, the signals accumulated in the sensor 330 are proportional to the integral value of the intensity of all light intensity peaks 221-229 observed during this phase (between the rising edge 241 and the falling edge 242 of the control signal 240), including the shorter peaks 230 occurring during the descending ramps 206 of the supply current 200.

As an example, the optical cavity 180 has arms 20 cm in length. The cavity modes are then 0.0125 cm−1 apart. The variable component 204 may represent 15% of the DC component 202 of the power supply current for the laser source 100, which allows sweeping about 40 cavity modes. The spectrometer 330 may comprise 1024 pixels and cover a frequency band from 250 cm−1 to 2500 cm−1. Its spectral resolution is therefore 10 cm−1. The forty or so cavity modes swept are therefore less than a quarter of the spectral width per pixel. The fact that the excitation source is non-monochromatic therefore has a negligible effect on the performance of the Raman spectrometer, compared to a purely monochromatic excitation source. It can be observed that the robustness of the system is not affected if only less than ten cavity modes are swept. The period of the variable component 204 may be between 0.05 s and 0.2 s, the minimum value being reached when the sweeping speed becomes too high and impacts the amplitude of the light intensity peaks in the cavity. The duration of the exposure phases of the sensor 330 may then be between 10 and a few hundred periods of the variable component 204, i.e., a fraction of a second to a few tens of seconds, depending on the intensity of the Raman signal. If the length of the arms of the optical cavity 180 is reduced to 10 cm, a variable component 204 of 15% of the DC component 202 of the supply current for the laser source 100 allows sweeping about twenty cavity modes. The impact of this sweep on the spectral resolution of the spectrometer remains unchanged, however.

Figure 3:
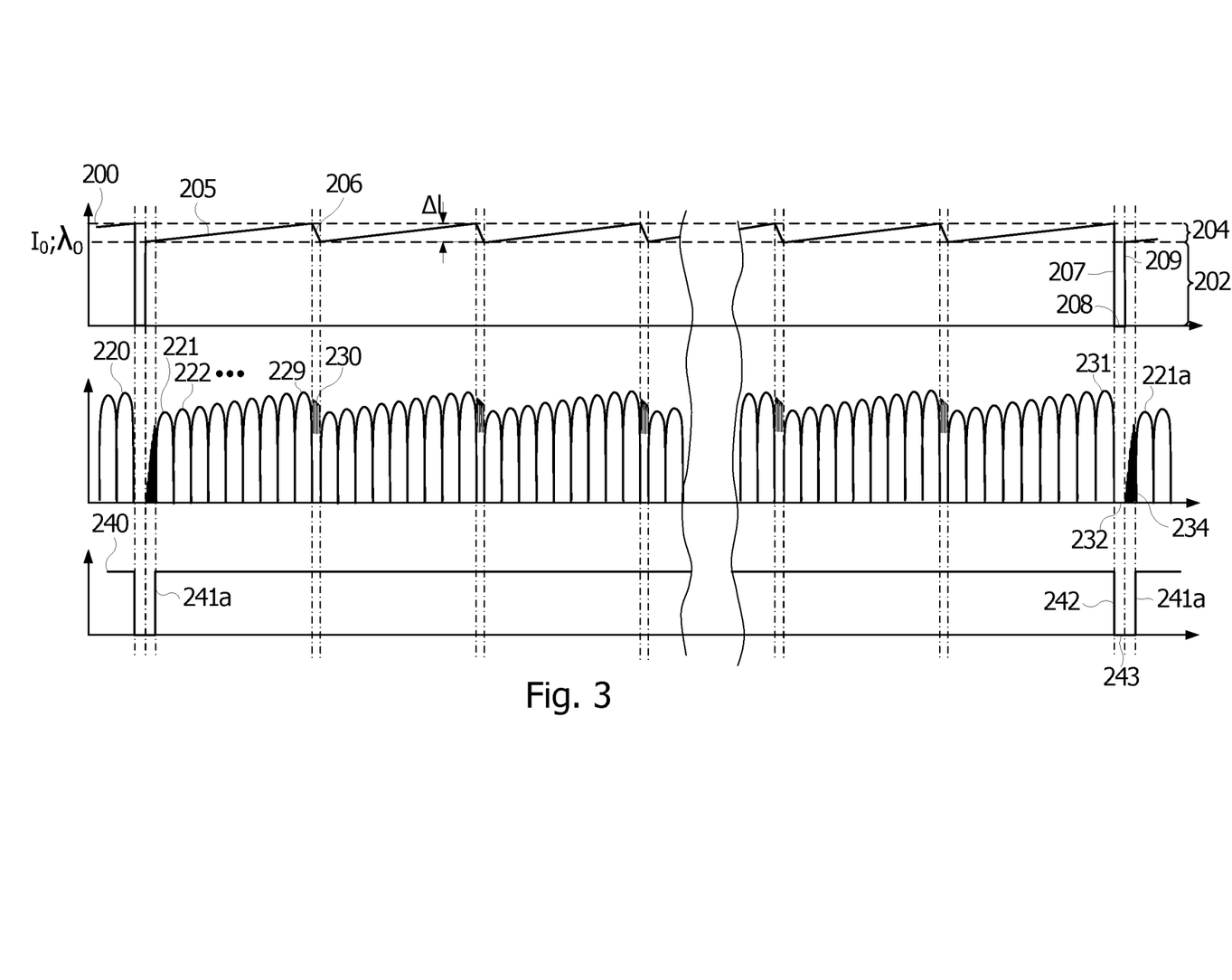

According to an embodiment, the supply current 200 is cancelled at the end of the exposure phase of the sensor 330, marked by the falling edge 242 of signal 240. Thus, as illustrated in FIG. 3, the supply current 200 is set to zero during the period 208 between the edges 207 and 209. At the rising edge 209, the supply current resumes the value I0 (202).

Consider the case where the end of the exposure phase of sensor 330 is triggered at the end of a rising ramp. During the time 208 when the laser source is off, between the edges 207 and 209, a part 232 of the signal 220 provided by the photodetector 190 corresponds to a measurement in the absence of light. This measurement is stored for subsequent subtraction from all measurements of the signal 220 provided by the photodetector 190. Thus, in FIG. 3, the corrected signal 220 is zero during the period 232 following the peak 231, corresponding to the period 208 when the laser source 100 is off. This arrangement offers correction for drifts in the photodetector 190, which provides a dark signal measurement (dark current) in the absence of light, as this measurement may vary as a function of time.

From the time 209 when the supply current for the laser source 100 is restored to the value I0, the beam power in the cavity 180 takes some time to build up, which is shown on the waveform 234 in the signal 220. This is a result of the junction temperature of the laser source 100 dropping a few degrees below its nominal operating temperature, due to its power being turned off. Thus, the laser source 100 starts by emitting a wavelength shorter than that of the first light intensity peak 221, and then the emitted wavelength increases until it reaches the wavelength corresponding to the first light intensity peak 221, producing a waveform 234 including successive excitations of cavity resonance modes at wavelengths shorter than the swept wavelength band. It turns out that such excitations can "pollute" the measurements made by the spectrometer.

According to an embodiment, this pollution phenomenon resulting from powering off the laser source 200 in view of updating the dark signal measurement of the photodetector 190, is avoided by postponing the beginning 241 of the exposure phase of the sensor 330 to the beginning of the appearance of the first peak 221 (or 221a), i.e., to the time 241a. Of course, the frequency of the power-off phases 208 of the supply current for the laser source 100 is adapted to the rate of change of the dark signal of the photodetector 190.

Figure 4:
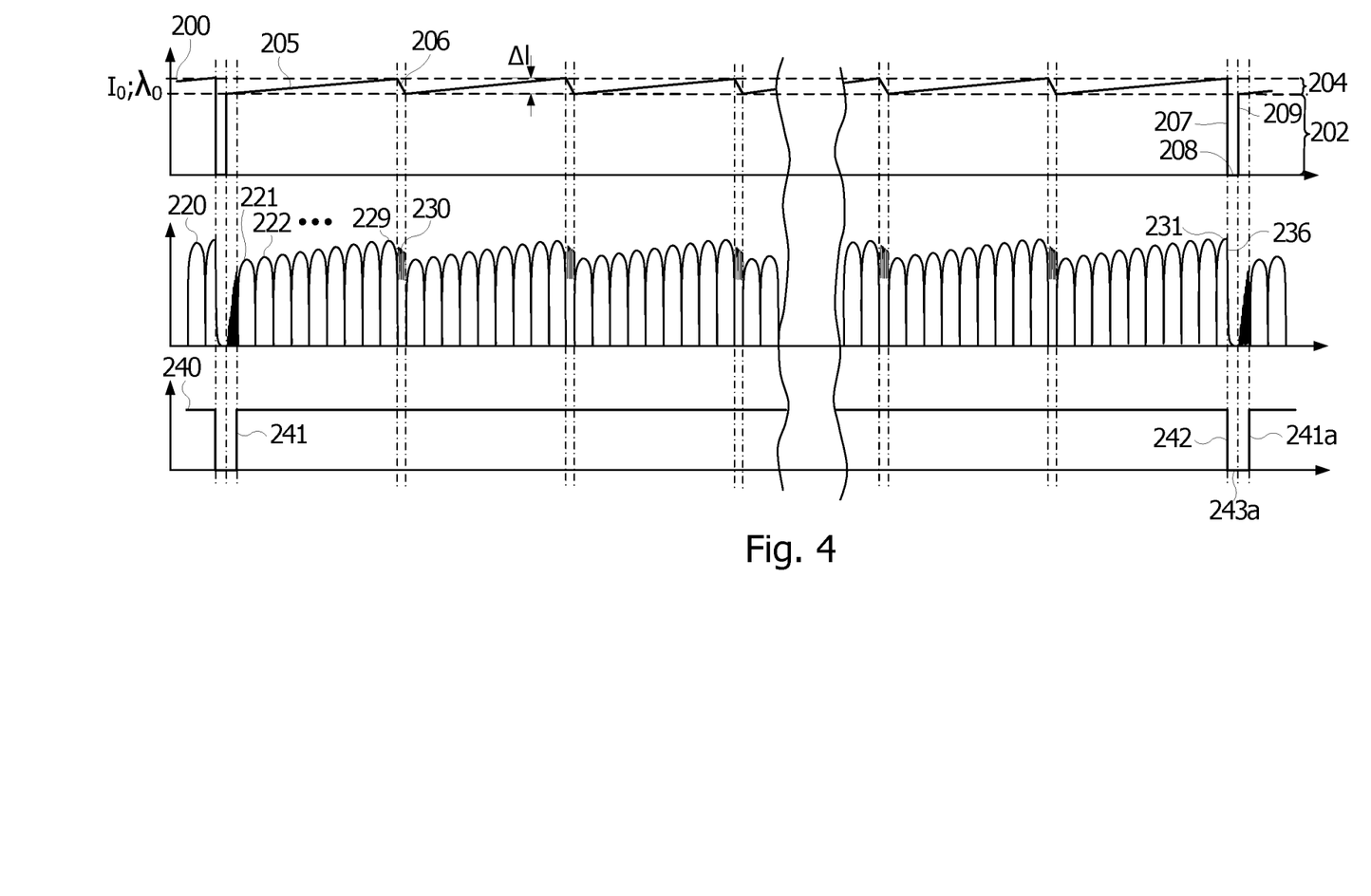

The power-off phase 208 of the supply current 200 for the laser source 100 may occur at a time when a laser beam of a certain intensity is present in the cavity 180. This case is illustrated in FIG. 4. The accumulated power in cavity 180 cannot disappear instantaneously, even if laser source 100 is no longer transmitting. In fact, the accumulated beam power in cavity 180 decreases exponentially until it disappears, as shown by the shape of signal 236, with a decay time constant τ that depends on the losses of the cavity mirrors 182, 184, 186 and the absorption of gases in the cavity. When the mirrors have very high reflectivity, the time constant τ may range from a fraction of a microsecond to several hundred microseconds.

According to an embodiment, the power supply for the laser source 100 is switched off at the time when the last peak 231 of signal 220 reaches its maximum value, this last peak occurring at the end of a rising ramp 205 of the supply current 200. This operation makes available information on the condition of the cavity 180. Indeed, in an application to gas analysis, dust or corrosive products may affect the reflectivity of the cavity mirrors 182, 184, 186. Indeed, it turns out that the decay time of the signal 220 after switching off the supply current 200 is representative of the losses in the cavity and thus of the condition of the cavity mirrors. If this decay time is measured too high, an alarm may be triggered to indicate that the cavity mirrors need to be cleaned. After a waiting time sufficient to ensure that decay is complete, several measurements of the signal 220 from the photodetector 190 may be acquired, and then the dark current may be determined by averaging these measurements.

In addition, the pixel circuits of spectrometer sensors such as CCDs also produce dark signals that can vary over time and from one pixel circuit to another. These signals induce noise that limits the resolution and sensitivity of the Raman spectrometer. The dark signal from each pixel circuit has a random component that changes with each exposure phase of the sensor 330. This random component is due primarily to thermal noise appearing in the light-sensitive cells of the pixel circuits, and in the readout circuits RDC of the sensor 330. However, this random component remains quite small and may be reduced by averaging in proportion to the square root of the number of averaged exposures. The pixel circuits of all spectrometer sensors have a dark current with a fixed component that varies from pixel to pixel and is related to the manufacturing process of the sensor 330. This fixed component may reach significant values. The fixed components of the dark currents of all the pixel circuits of a spectrometer sensor form a fixed pattern noise or FPN that significantly degrades the sensitivity of the system. Typically, the FPN for a spectrometer sensor is predetermined and prerecorded, and subtracted from the pixel signals provided by sensor 330. However, it turns out that the FPN of a sensor changes over time, particularly due to aging of the components of the sensor 330, so multiple exposures in the absence of light should be made periodically to calculate average values. Typically, the FPN should be refreshed with a periodicity of a few hours depending on the stability of the system. In Raman spectrometry applied to gaseous media requiring the capture of weak scattered light signals, exposure times are generally long, of the order of several tens of seconds, and sometimes more, especially when measurements from several exposures are averaged. It is not desirable, especially in process control applications, to interrupt the acquisition of measurements for several minutes to refresh the FPN.

According to an embodiment, an initial FPN is determined during a spectrometer startup procedure based on a sufficient number of exposures in the absence of light. During operation of the spectrometer, smaller numbers of measurements of the dark signal with the laser turned off are made and combined with the initial or previous FPN values, for example by a sliding average calculation. For example, dark signal determination may be performed periodically, after several tens of consecutive exposure phases for Raman signal measurement. A dark signal measurement may involve turning off the power to the laser source 100 during a shutdown phase extending over one or more consecutive exposure phases. During this shutdown phase, a dark current measurement is acquired for each light-sensitive cell of the spectrometer sensor 330 by reading the cell. Each measurement is used to correct a stored average dark current value for the corresponding photosensitive cell, for example by a sliding average calculation. The average dark current value of each photosensitive cell is used to correct each spectrum measurement provided by the photosensitive cell.

According to an embodiment, the dark current measurements in the photosensitive cells are preceded by several successive measurements not taken into account, carried out at the beginning of the shutdown phase, in order to erase the photosensitive cells, i.e. in order to ensure that the electric charges accumulated in the photosensitive cells during the exposure phases preceding the shutdown phase have been evacuated.

In the configuration shown in FIG. 1, the light scattered in the optical cavity is observed by the optical device 50 substantially perpendicular to the propagation direction of the beam 172, 173 in the cavity 180. The arrangements previously described with reference to FIG. 1 also apply to the case of coaxial observation where the light scattered in the optical cavity is observed along the axis of the beam 172 or 174 through the mirror 184 or 186.

According to an embodiment, the observation of the light scattered in the optical cavity 180, is coaxial, and the two cavity end mirrors 184, 186 have a maximum reflection coefficient in a wavelength band including the wavelengths of the excited cavity resonance modes (peaks 221-229), and a maximum transmission coefficient outside this wavelength band. There are indeed coatings called "notch filters" having this property. In this way, the excitation wavelengths of the cavity (excitation light and light elastically scattered in the optical cavity) are reflected by the mirrors 184, 186, while the light inelastically scattered in the cavity (Raman signals including the Stokes and anti-Stokes lines) is transmitted by these mirrors to the spectrometer. There are also coatings called "edge filters" with a maximum reflection coefficient up to a certain wavelength from which the transmission coefficient is maximum. With such a coating, the excitation wavelengths of the cavity are reflected by the mirrors 184, 186, while only the Stokes (or anti-Stokes) lines are transmitted by these mirrors to the spectrometer. This coaxial collection mode has the advantage of providing a more intense Raman signal. However, in a system with an optical cavity excited by a laser diode, this coaxial collection mode leads to the appearance of an amplified spontaneous emission (ASE), likely to mask the Raman signals, this emission resulting from the use of a laser diode. The use of such mirror coatings prevents the resonance of the amplified spontaneous emission.

In order to obtain quantitatively meaningful spectrum measurements, variations in the accumulated optical power in the cavity due to variations in the composition of the gases present in the cavity, contamination of the cavity mirrors, and misalignments in the injection of the laser beam into the cavity must be taken into account. For this purpose, a normalization of the spectrum measurements is performed. This normalization can be performed as a function of the integral value of the light intensity measurements provided by the photodetector 190, for example by dividing each of the spectrum measurements obtained at the end of the exposure phase as a function of the integral value of the light intensity measurements of the laser beam in the optical cavity.

According to an embodiment, a portion of the scattered light in the optical cavity received by the optical device 50 is routed to an additional photodetector to measure variations in the light intensity of the scattered light. Knowing that the intensity of the elastically scattered light is very large compared to that of the inelastically scattered light, the measurements thus obtained represent essentially the elastically scattered light. An integral value of these measurements is then determined and may be used to normalize the spectrum measurements provided by the light-sensitive cells of the sensor 330, for example by dividing each of these measurements by the integral value. In practice, the light received by the additional photodetector includes an elastic (Raleigh) scattering component and an inelastic (Raman) scattering component. The Raman scattering component is several orders of magnitude smaller than the Rayleigh component, and can therefore be neglected. Since the Rayleigh and Raman components are collected in the same volume, it is possible to determine the value of the total photon flux at the excitation wavelength, relative to a calibration value obtained at the time of system calibration, and thus obtain a normalized Raman spectrum, both independent of variations in the intensity of the excitation beam in the cavity, and independent of possible misalignments between the scattered light collection device and the excitation beam in the cavity. The link between the Rayleigh component and the gas composition in the cavity is taken into account by considering the relative concentrations of the gases determined from the Raman spectrum. It should be noted that the contribution of the Raman component in the measured scattered light can be compensated by applying to the total value of the measured light intensity, a correction factor calculated according to a known ratio between the Rayleigh and Raman cross sections.

The portion of the scattered light transmitted to the additional photodetector may be extracted from the scattered light transmitted to the sensor 330 using a Y-coupler (in the case of perpendicular or coaxial observation), or using a dedicated optical fiber coupled to the output of the optical device 50 (in the case of perpendicular observation).

According to an embodiment, the integral values obtained for the photodiode 190 and for the additional photodetector are compared, for example by calculating the ratio between these two integral values, to determine any misalignment of the optical device 50 with the laser beam in the optical cavity. By comparing this ratio to a threshold value, it is possible to determine when this misalignment is excessive.

It is thus possible to continuously monitor the evolution of the system's operating parameters, to correct drifts in real time, without having to interrupt the gas measurements in the cavity, and to signal when it is no longer possible to obtain reliable measurements. As a result, the gas analysis system described above may be used in critical applications, such as the control of industrial processes, especially in the oil sector, and the control of anesthetic gases in the medical sector, or in highly disturbed environments (vibrations, ambient temperature variations).

Typically, signal acquisition by the sensor 330 is controlled by a separate processor with its own clock. As a result, the start and end of the exposure phases may occur at arbitrary times in the control signal 200. This lack of synchronization may lead to inconsistencies between the integrated reference signal provided by the photodetector 190 and the amounts of scattered light accumulated in the sensor 33 during the exposure phases. These inconsistencies may significantly affect the quality of the Raman signal normalization. This deterioration in normalization quality can be avoided by establishing a link between the exposure phases and the rising and falling phases of the control signal 200, and by implementing the following procedure, illustrated in FIG. 5.

Figure 5:
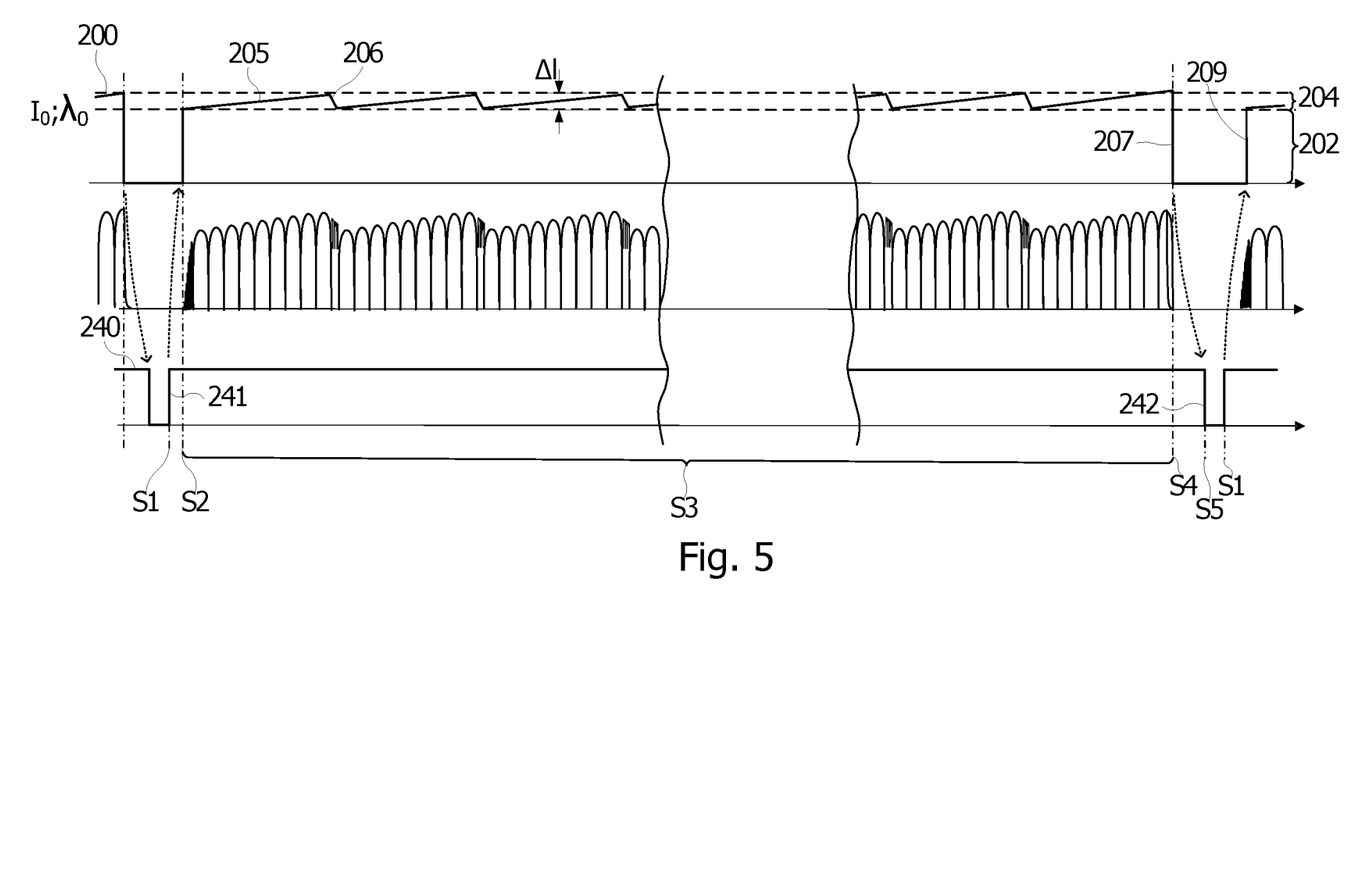

According to this procedure, the duration of the exposure phase of the sensor 330 is set to a value equal to an integer number Nrp of periods of the control signal 200, plus a fraction of this period. Before starting the exposure phase (accumulation of Raman light in the sensor 330), the control signal 200 is held at zero. This ensures that no light is present in the cavity 180. At the beginning of a step S1, an exposure phase start signal 241 is sent to a sensor control unit 330. A step S2 is triggered after a certain delay to ensure that the exposure of the sensor 330 has started. In step S2, the laser source 100 is turned on by applying the periodic control signal 200 to it. Nrp periods of the control signal 200 are applied to the laser source during a step S3. The sensor 330 then receives the Raman signal. The end of the period Nrp of the control signal 200 marks the end of step S3 and the beginning of step S4. In step S4, the control signal 200 is set to zero. The exposure phase of the sensor 330 continues for the fraction of the period of the control signal 200, until a step S5, while no Raman light is present in the cavity. During steps S1 through S5, the signal from the photodetector 190 is integrated, until a signal is received to end the exposure phase of the sensor 330. This procedure ensures that the Raman signal accumulated in the sensor 330 is proportional to the integrated signal from the photodetector 190, and is normalized without bias. Receipt of the signal 242 marking the end of the exposure phase in step S5 triggers a new step S1.

It will be clear to the person skilled in the art that the present disclosure is susceptible of various alternatives and various applications. In particular, the various optical components described above have been presented by way of example and depend essentially on the characteristics of the laser beam emitted by the laser source and thus on the choice of laser source. Obviously, if the characteristics of this beam are different, some of the optical components described may be unnecessary or even inappropriate, and other optical components may be necessary. What matters is that the characteristics of the laser beam at the entrance to the optical cavity are as close as possible to ideal characteristics, namely a circular cross-section (zero eccentricity) and divergences in all directions corresponding to that of the fundamental mode of the optical cavity. Indeed, the definition of means achieving such characteristics enters completely in the field of traditional design techniques of optical systems. In addition, the laser source may be designed to produce a laser beam with characteristics close to or corresponding to the ideal characteristics, so that one or another, or even all of the optical modules 110, 120, and 130 are not required.

Similarly, other devices known to adjust the phase and intensity of a light beam may be used to adjust the phase and intensity of the feedback beam.

Furthermore, it may be envisaged to transmit the laser beam issued by the laser source and the feedback beam through different optical paths between the laser source and the entrance of the cavity. This arrangement simplifies the device for adjusting the intensity of the feedback beam, which then does not need to be crossed by the laser beam from the laser source, without acting on the latter.

Furthermore, it will be clear to the skilled person that the use of a V-cavity is not necessary. For example, a linear cavity with two mirrors combined with the arrangements described in references [4] and [5] to implement optical feedback, or optical feedback locked by a spatial offset of the laser diode, as described in U.S. Pat. No. 5,835,522, may be implemented within the scope of the present disclosure.

CITED REFERENCES

[1] "An Efficient Intracavity Laser Raman Spectrometer", M. Hercher et. al, Applied Spectroscopy 32, No 3, pp 298-301 (1978);

[2] "Frequency Stabilization of Semi-conductor lasers by resonant optical feedback", Dahmani et al, Opt. Lett. 12, pp. 876-878 (1987);

[3] "Optically Self-Locked Semiconductor Laser with Servo Control for Feedback Phase and Laser Current", Peter Buch et al, IEEE Journal of Quantum Electronics, vol. 27 (7), pp. 1863-1868 (1991);

[4] "Cavity-enhanced resonant photoacoustic spectroscopy with optical feedback cw diode lasers: A novel technique for ultratrace gas analysis and high-resolution spectroscopy", M. Hippler, C. Mohr, K. A. Keen, E. D. McNaghten, The Journal of Chemical Physics 133, 044308 (2010);

[5] "Cavity-Enhanced Raman Spectroscopy of Natural Gas with Optical Feedback cw-Diode Lasers", M. Hippler, Anal. Chem. 87, 7803-7809 (2015);

The invention claimed is:

1. A method for analyzing gas by Raman spectrometry, the method comprising:
applying a control signal to a laser source to produce a laser beam sweeping a range of frequencies including frequencies of multiple resonant modes of an optical cavity holding gases to be analyzed, the width of the frequency range being less than the resolution of a Raman spectrometer,
supplying the laser beam to an entrance of the optical cavity,
extracting a feedback beam from the optical cavity,
adjusting a phase and an amplitude of the feedback beam,
sending the phase and amplitude adjusted feedback beam to the laser source,
during sweeping of the frequency range, measuring light intensity variations of the laser beam in the optical cavity, and detecting light intensity peaks in the light intensity variations, each light intensity peak corresponding to a resonance mode of the optical cavity, the phase of the feedback beam being adjusted to reduce a deviation between a median time and the time of occurrence of an apex of one of the light intensity peaks, the amplitude of the feedback beam being adjusted to reduce at least an interval of zero intensity between the light intensity peaks, and
acquiring, with a spectrometer sensor, measurements of the spectrum of light inelastically scattered by the laser beam in the optical cavity to determine the nature and/or concentration of gases in the optical cavity.

2. The method of claim 1, wherein:
the control signal of the laser source has a periodic shape, and
the spectrometer sensor, comprising a plurality of photosensitive cells, receives a portion of the inelastically scattered light and is controlled to operate exposure phases alternating with readout phases during which spectrum measurements are produced by the photosensitive cells,
the method comprising, during each exposure phase:
obtaining an integral value of measurements of light intensity of the laser beam in the optical cavity, and/or of light intensity of a portion of the light elastically scattered by the laser beam in the optical cavity, and
normalizing each of the spectrum measurements obtained at the end of the exposure phase as a function of the integral value, to produce a normalized spectrum.

3. The method of claim 2, wherein the exposure phases have a duration equal to a multiple of the period of the control signal of the laser source, plus a fraction of that period, the start of each exposure phase being synchronized with the control signal of the laser source.

4. The method of claim 2, wherein each exposure phase is started and interrupted during periods when no light is present in the optical cavity.

5. The method of claim 2, further comprising:
periodically turning off power to the laser source to measure a dark current in a photodetector providing the measurements of light intensity variations of the laser beam in the optical cavity, and
correcting the measurements of light intensity variations of the laser beam in the optical cavity using an average of the dark current measurements.

6. The method of claim 5, wherein the power interruptions of the laser source are performed outside the exposure phases.

7. The method of claim 2, further comprising:
turning off the power to the laser source during an interruption phase extending over at least one consecutive exposure phase, and
for each light sensitive cell of the spectrometer sensor:
measuring a dark current during the interruption phase,
correcting a stored average dark current for the photosensitive cell based on the dark current measurement obtained for the photosensitive cell, and
correcting each spectrum measurement provided by the photosensitive cell according to the stored average dark current for the photosensitive cell,
wherein the measurement of dark current may be preceded by several measurements not taken into account to erase the photosensitive cells.

8. The method of claim 1, wherein the laser beam provided at the entrance of the optical cavity and the feedback beam are transmitted through the same optical path between the laser source and the entrance of the optical cavity.

9. The method of claim 1, wherein the amplitude of the feedback beam is adjusted by an adjustable Faraday isolation module installed in the optical path between the laser source and the entrance of the optical cavity, the Faraday isolation module attenuating the amplitude of the feedback beam and passing the laser beam from the laser source.

10. The method of claim 9, wherein the Faraday isolation module is servo-controlled as a function of light intensity measurements of the laser beam in the optical cavity, to minimize the zero intensity intervals between light intensity peaks, wherein the servocontrol of the Faraday isolation module can be achieved by acting on its temperature.

11. A device for analyzing gas by Raman spectrometry, the device comprising an optical cavity into which a laser beam emitted by a laser source is introduced, the device further comprising:
a processor; and
a memory coupled to the processor, the memory comprising instructions that, when executed by the processor, cause the device to:
apply a control signal to the laser source to produce a laser beam sweeping a range of frequencies including frequencies of multiple resonant modes of an optical cavity holding gases to be analyzed, the width of the frequency range being less than the resolution of a Raman spectrometer, supply the laser beam to an entrance of the optical cavity, extract a feedback beam from the optical cavity, adjust a phase and an amplitude of the feedback beam, send the phase and amplitude adjusted feedback beam to the laser source, during sweeping of the frequency range, measure light intensity variations of the laser beam in the optical cavity, and detect light intensity peaks in the light intensity variations, each light intensity peak corresponding to a resonance mode of the optical cavity, the phase of the feedback beam being adjusted to reduce a deviation between a median time and the time of occurrence of an apex of one of the light intensity peaks, the amplitude of the feedback beam being adjusted to reduce at least an interval of zero intensity between the light intensity peaks, and acquire, with a spectrometer sensor, measurements of the spectrum of light inelastically scattered by the laser beam in the optical cavity to determine the nature and/or concentration of gases in the optical cavity.

12. The device of claim 11, wherein the laser source is configured to sweep the frequency range without mode hopping.

13. The device of claim 12, wherein the optical cavity is V-shaped and comprises a coupling mirror forming the entrance to the optical cavity, and two cavity end mirrors, the cavity end mirrors having a reflectivity greater than or the same as the coupling mirror.

14. The device of claim 11, wherein the mirrors forming the optical cavity have radii of curvature adapted to adjust the shape of the beam within the optical cavity to a zone for collecting light scattered in the cavity under the effect of the laser beam.

15. The device of claim 12, wherein light scattered in the optical cavity is observed through one of the cavity end mirrors, the cavity end mirrors having a coating with a maximum reflectance for the reflected beam in each of the resonance modes of the optical cavity, and having a maximum transmittance for at least one Stokes line of Raman lines.

16. The device of claim 11, wherein the laser source is one of the following types:
a distributed feedback laser diode,
a distributed Bragg reflector laser diode,
a Fabry-Perot type diode stabilized by a volume or holographic Bragg diffraction grating, or by a narrow band filter,
a laser associated with a device for adjusting the emission frequency,
a surface emitting laser with a vertical cavity, coupled to a dielectric membrane mirror.

17. The device of claim 11, comprising an actuator coupled to a mirror for altering an optical path length between the laser source and the entrance to the optical cavity, to adjust the phase of the feedback beam.

* * * * *